(12) United States Patent
Futashima et al.

(10) Patent No.: US 11,717,206 B2
(45) Date of Patent: Aug. 8, 2023

(54) BIOELECTRODE AND METHOD OF MANUFACTURING THE BIOELECTRODE

(71) Applicant: NOK CORPORATION, Tokyo (JP)

(72) Inventors: Ryo Futashima, Fujisawa (JP); Yasushi Sugiyama, Fujisawa (JP); Toru Uda, Fujisawa (JP)

(73) Assignee: NOK CORPORATION

( * ) Notice: Subject to any disclaimer, the term of this patent is extended or adjusted under 35 U.S.C. 154(b) by 1022 days.

(21) Appl. No.: 16/310,993

(22) PCT Filed: Jul. 5, 2017

(86) PCT No.: PCT/JP2017/024670
§ 371 (c)(1),
(2) Date: Dec. 18, 2018

(87) PCT Pub. No.: WO2018/008688
PCT Pub. Date: Jan. 11, 2018

(65) Prior Publication Data
US 2020/0305746 A1    Oct. 1, 2020

(30) Foreign Application Priority Data

Jul. 6, 2016    (JP) ................. 2016-134492

(51) Int. Cl.
*A61B 5/00* (2006.01)
*A61B 5/25* (2021.01)

(52) U.S. Cl.
CPC ........ *A61B 5/25* (2021.01); *A61B 2562/0215* (2017.08); *A61B 2562/125* (2013.01)

(58) Field of Classification Search
CPC ...... A61N 1/05; A61N 1/0492; A61N 1/0529; A61N 1/0531; A61N 1/36017; A61N 1/04;
(Continued)

(56) References Cited

U.S. PATENT DOCUMENTS 4,524,087 A    6/1985    Engel
5,330,527 A *  7/1994    Montecalvo ......... A61B 8/4281
                                            252/500
(Continued)

FOREIGN PATENT DOCUMENTS

CN    1145037 A    3/1997
CN    1475865 A    2/2004
(Continued)

OTHER PUBLICATIONS

Chlaihawi et al. "Screen Printed MWCNT/PDMS Based Dry Electrode Sensor for Electrocardiogram (ECG) Measurements" published in IEEE International Conference on Electro/Information Technology. (Year: 2015).*
(Continued)

*Primary Examiner* — Joseph A Stoklosa
*Assistant Examiner* — Brian M Antiskay
(74) *Attorney, Agent, or Firm* — Harness, Dickey & Pierce, P.L.C.

(57) ABSTRACT

An object of the present invention is to provide a bioelectrode, which can stably measure biological information and is suitable for repeated use, and a method of manufacturing the bioelectrode. This object is solved by a bioelectrode comprising a silver coating layer provided on a conductive silicone rubber electrode, wherein the conductive silicone rubber electrode is composed of a silicone rubber containing conductive carbon particles, the silver coating layer is composed of silicone rubber and at least one of agglomerated silver powder and flake-like silver powder, and the silver coating layer has a thickness of 18 μm to 80 μm, and, preferably, in which the silver powder contains both the agglomerated silver powder and the flake-like silver powder.

3 Claims, 5 Drawing Sheets

(58) Field of Classification Search
CPC .. A61N 1/0456; A61N 1/0526; A61N 1/0534; A61N 1/0541; A61N 1/054; A61N 1/0484; A61B 5/25; A61B 5/282; A61B 5/0245; A61B 5/291; B22F 1/00
USPC ........ 600/372, 382–393, 508–509, 544–545; 607/115–118
See application file for complete search history.

(56) References Cited

U.S. PATENT DOCUMENTS

| | | | | |
|---|---|---|---|---|
| 5,370,116 | A * | 12/1994 | Rollman | A61B 5/303 600/382 |
| 5,427,096 | A * | 6/1995 | Bogusiewicz | A61N 1/0452 600/396 |
| 5,611,339 | A | 3/1997 | Okabe et al. | |
| 7,476,222 | B2 | 1/2009 | Sun et al. | |
| 10,176,903 | B2 | 1/2019 | Sekitani et al. | |
| 2003/0134545 | A1 * | 7/2003 | McAdams | A61N 1/0492 600/372 |
| 2004/0135129 | A1 | 7/2004 | Hattori et al. | |
| 2005/0004509 | A1 | 1/2005 | Sun et al. | |
| 2005/0015134 | A1 * | 1/2005 | Carim | A61N 1/0492 607/142 |
| 2006/0004273 | A1 * | 1/2006 | Lobodzinski | A61B 5/25 600/397 |
| 2007/0282408 | A1 * | 12/2007 | Coggins | A61B 5/25 607/115 |
| 2011/0230749 | A1 * | 9/2011 | Chan | C08L 83/04 264/105 |
| 2013/0131460 | A1 | 5/2013 | Yuen | |
| 2013/0225966 | A1 | 8/2013 | Macia Barber et al. | |
| 2014/0303470 | A1 | 10/2014 | Tsukada et al. | |
| 2015/0148646 | A1 | 5/2015 | Park et al. | |
| 2017/0169914 | A1 | 6/2017 | Sekitani et al. | |
| 2017/0188949 | A1 | 7/2017 | Macia Barber et al. | |
| 2017/0332928 | A1 * | 11/2017 | Atashbar | A61B 5/25 |
| 2018/0215941 | A1 * | 8/2018 | Hagar | H01B 1/22 |
| 2019/0066866 | A1 | 2/2019 | Tsukada et al. | |

FOREIGN PATENT DOCUMENTS

| | | |
|---|---|---|
| CN | 102178521 A | 9/2011 |
| CN | 102858236 A | 1/2013 |
| CN | 103379851 A | 10/2013 |
| CN | 103930612 A | 7/2014 |
| CN | 104665806 A | 6/2015 |
| EP | 0 085 327 A1 | 8/1983 |
| JP | S58-135506 A | 8/1983 |
| JP | H01-164099 A | 6/1989 |
| JP | H02-174831 A | 7/1990 |
| JP | H05-095924 A | 4/1993 |
| JP | H09-168518 A | 6/1997 |
| JP | 2003-220043 A | 8/2003 |
| JP | 2003-225217 A | 8/2003 |
| JP | 2007-173226 A | 7/2007 |
| JP | 2014-108134 A | 6/2014 |
| WO | 2015-100499 A1 | 7/2015 |
| WO | WO-2015/119217 A1 | 8/2015 |

OTHER PUBLICATIONS

Matsuo, Tadayuki: "Properties of Recording Electrodes Connected through the Input Impedance of Bioelectric Amplifier"; Japanese Journal of Medical Electronics and Biological Engineering; Oct. 1970; vol. 8; No. 5; pp. 11-16.
International Preliminary Report on Patentability and Written Opinion for Patent Application No. PCT/JP2017/024670 dated Sep. 25, 2017, with English translation (24 pages).
Extended European Search Report for Application No. 17824291.3 dated Jul. 3, 2020 (11 pages).
2nd Office Action for corresponding Chinese Application No. 201780040465.1 dated Sep. 14, 2021 with English translation (30 Pages).
J-P Uldry et al., "Developing Conductive Elastomers for Applications in Robotic Tactile Sensing", Advanced Robotics, vol. 6, No. 2, pp. 255-271 (1992).
Partial Supplementary European Search Report for Patent Application No. EP 17824291.3 dated Dec. 19, 2019 (14 pages).
Decision of Refusal dated Mar. 29, 2021 in the corresponding Japanese Application No. 2017-561788 with English translation (8 pages).
Extended European Search Report for corresponding Application No. EP 21 154 215.4 dated Apr. 14, 2021 (8 pages).
1st Office Action dated Apr. 15, 2021 in the corresponding Chinese Application No. 201780040465.1 with English translation (31 pages).
Notice of Reasons for Refusal dated Dec. 14, 2020 in the corresponding JP application No. 2017-561788 with English translation (12 Pages).
The Japanese Journal of Medical Instrumentation; vol. 80; No. 1 (2010); pp. 28-37.
Hoshimiya, Nozomu: "Important factors of the bioelectrodes"; Shindenzu, 1984; vol. 4; No. 1; pp. 3-10.
Takeda, Sunao: "Tokushu Seitai o Hakaru Denkyoku Sensor"; BME; 1987; vol. 1; No. 10; pp. 47-58.

* cited by examiner

BIOELECTRODE AND METHOD OF MANUFACTURING THE BIOELECTRODE

CROSS REFERENCE TO RELATED APPLICATIONS

This application is a U.S. National Stage Application of International Application No. PCT/JP2017/024670, filed on Jul. 5, 2017, and published in Japanese as WO 2018/008688 on Jan. 11, 2018, and claims priority to Japanese Patent Application No. 2016-134492, filed on Jul. 6, 2016. The entire disclosures of the above applications are incorporated herein by reference.

BACKGROUND

Technical Field

The present invention relates a bioelectrode and a method of manufacturing the bioelectrode and relates particularly to a bioelectrode, which can stably measure biological information and is suitable for repeated use, and a method of manufacturing the bioelectrode.

Related Art

In medical facilities and nursing care facilities, biological information is measured to ascertain a health condition of a subject. For example, when biological information is measured during sleeping, a bioelectrode with reduced discomfort in wearing is required so as not to disturb the subject's sleeping. In order to avoid sudden death due to heart attack and the like and the risk of other health problems, there is an increasing demand for constant measurement of biological information such as heartbeat and electrocardiogram. Even for healthy people, grasping the state of the body and mind through measurement of biological information is important for maintaining health. In response to such demand, a bioelectrode which causes no discomfort even when firmly adhering for a long time is required.

Conventionally, as a bioelectrode material, a thin plate of highly conductive metal such as aluminum, gold, silver, platinum, or copper has been used.

However, these metallic bioelectrode materials have poor adhesion to the skin and insufficient detection of electric signals from the skin, so that it is necessary to apply gel, cream, paste or the like to the skin.

Moreover, when a metallic bioelectrode is used after applying gel, cream, paste or the like, although the metallic bioelectrode is improved in terms of electric signal detection, since the metal is hard, the metallic bioelectrode is inadequate to firmly adhere for a long time.

As for a bioelectrode formed of an adhesive such as gel, there is one disclosed in The Japanese Journal of Medical Instrumentation, Vol. 80, No. 1 (2010) pp. 28-37, and although there is no need to apply gel, cream, paste or the like, dirt and dust tend to adhere to the adhesive to gradually lose tackiness, so that there is a problem with repeated use.

As an example of a bioelectrode which causes no discomfort even when firmly adhering for a long time, there is cloth made of conductive fibers (JP-2003-220043).

However, JP-2003-220043 has a problem in that noise caused by instability of contact with the skin is large.

There is exemplified a method in which a conductive polymer is coated on a fiber surface to achieve stable measurement (JP-2014-108134).

However, in JP-2014-108134, the production cost of the conductive polymer is high, and there is also a problem in durability.

An electrode formed of flexible rubber can be repeatedly used, and adhesiveness with the skin is good.

However, in conductive rubber including carbon-based particles, contact impedance with the skin is high because of an electrolytic solution containing salt and water on the human body surface, so that measurement becomes unstable (JP-H5-95924).

The reason why the measurement in JP-H5-95924 is unstable is that an electric double layer in which positive and negative charges are distributed at a boundary between an electrode and an electrolytic solution is formed and a potential difference (polarization voltage) is generated, which becomes resistance (The Japanese Journal of Medical Instrumentation).

There is a method of stabilizing measurement by using an antistatic agent including metal ions in conductive rubber using carbon-based particles (JP-2003-225217).

However, in JP-2003-225217, since a bioelectrode firmly adheres to the skin, water and detergent are indispensable for repeated use. Since the antistatic agent is highly soluble in water, the antistatic agent on an electrode surface is lost along with repeated use, and there is a problem in that measurement becomes gradually unstable.

Since carbon-based conductive rubber is used also in a system using an antistatic agent, there is a problem in that contact impedance with the skin is high.

Thus, an object of the present invention is to provide a bioelectrode, which can stably measure biological information and is suitable for repeated use, and a method of manufacturing the bioelectrode.

Other objects of the present invention will be apparent from the following description.

SUMMARY OF THE INVENTION

The objects of the present invention will be solved by the following inventions.

In a first aspect, a bioelectrode comprises a silver coating layer provided on a conductive silicone rubber electrode,
wherein
the conductive silicone rubber electrode is composed of a silicone rubber containing conductive carbon particles,
the silver coating layer is composed of silicone rubber and at least one of agglomerated silver powder and flake-like silver powder, and
the silver coating layer has a thickness of 18 µm to 80 µm.

In a second aspect, a bioelectrode comprises a silver coating layer provided on a conductive silicone rubber electrode,
wherein
the conductive silicone rubber electrode is composed of a silicone rubber containing conductive carbon particles,
the silver coating layer is composed of silicone rubber and at least one of agglomerated silver powder and flake-like silver powder, and
the silver coating layer has electrical conductivity and ionic conductivity.

In a third aspect, in the bioelectrode according to the second aspect, ions exist between particles of the silver powder to allow the silver coating layer to have the ionic conductivity.

In a fourth aspect, in the bioelectrode according to the second or third aspects, the silver coating layer has a thickness of 18 µm to 80 µm.

In a fifth aspect, in the bioelectrode according to any one of the first to fourth aspects, the silver powder comprises both the agglomerated silver powder and the flake-like silver powder.

In a sixth aspect, in the bioelectrode according to any one of the first to fifth aspects, a flexible printed wiring board is provided as a signal transmission member on a surface opposite to a surface provided with the silver coating layer on the conductive silicone rubber electrode.

In a seventh aspect, a method of manufacturing a bioelectrode, the method comprises:

preparing a conductive silicone rubber electrode composed of a silicone rubber containing conductive carbon particles;

applying a silver paste comprising silicone rubber and at least one of agglomerated silver powder and flake-like silver powder on the conductive silicone rubber electrode; and curing the silver paste to form a silver coating layer having a thickness of 18 μm to 80 μm.

In an eighth aspect, a method of manufacturing a bioelectrode, the method comprises:

preparing a conductive silicone rubber electrode composed of a silicone rubber containing conductive carbon particles;

applying and curing a silver paste comprising silicone rubber and at least one of agglomerated silver powder and flake-like silver powder on the conductive silicone rubber electrode to form a silver coating layer having electrical conductivity; and imparting ionic conductivity to the silver coating layer by causing ions to exist between particles of the silver powder of the silver coating layer.

In a ninth aspect, in the method of manufacturing the bioelectrode according to the eighth aspect, the ionic conductivity is imparted by immersing the silver coating layer in a solution prepared by dissolving at least one inorganic salt selected from chloride salt, sulfate, and carbonate.

In a tenth aspect, in the method of manufacturing the bioelectrode according to the ninth aspect, the inorganic salt is a chloride salt of alkali metal.

In an eleventh aspect, in the method of manufacturing the bioelectrode according to any one of the eighth to tenth aspects, the applying and the curing are performed such that the silver coating layer has a thickness of 18 μm to 80 μm.

In a twelfth aspect, in the method of manufacturing the bioelectrode according to any one of the seventh to eleventh aspects, the silver powder comprises both the agglomerated silver powder and the flake-like silver powder.

In a thirteenth aspect, in the method of manufacturing the bioelectrode according to any one of the seventh to twelfth aspects, the conductive silicone rubber electrode is formed directly on a flexible printed wiring board, as a signal transmission member, so that the flexible printed wiring board is provided on a surface opposite to a surface to be provided with the silver coating layer on the conductive silicone rubber electrode.

Effect of the Invention

The present invention can provide a bioelectrode, which can stably measure biological information and is suitable for repeated use, and a method of manufacturing the bioelectrode.

DETAILED DESCRIPTION OF THE PREFERRED EMBODIMENTS

Hereinafter, embodiments of the present invention will be described with reference to the drawings.

1. First Embodiment

Bioelectrode

Figure 1:
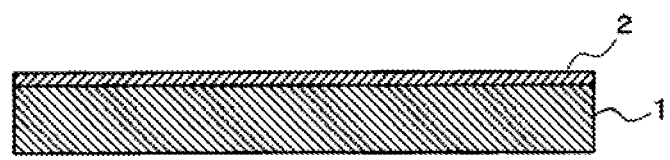
FIG. 1 is a schematic sectional view explaining an example of a bioelectrode of the present invention.

As illustrated in FIG. 1, a bioelectrode (also referred to as a biomedical electrode) of the first embodiment of the present invention has, on a conductive silicone rubber electrode 1 obtained by using conductive carbon particles in silicone rubber, a silver coating layer 2 containing at least one of agglomerated silver powder and flake-like silver powder and silicone rubber, and the silver coating layer has a thickness of 18 μm to 80 μm.

The bioelectrode thus configured includes the silver coating layer 2 on a surface in contact with a living body and therefore can achieve the electrical conduction by silver, and since this bioelectrode is a rubber flexible electrode, the bioelectrode has good adhesion to the living body and does not give an unpleasant feeling even if the bioelectrode firmly adheres for a long time.

When the silver coating layer 2 contains silicone rubber as a binder together with the silver powder, high adhesion to the conductive silicone rubber electrode 1 is exhibited, and peeling is prevented, so that contact impedance with a living body can be suitably reduced. Thus, effects can be obtained that biological information can be stably measured and it is suitable for repeated use.

Since there is no need to use a gel or the like at this time, stable measurement can be achieved even under dry conditions, and the method of use is simple.

Most of the bioelectrode can be constituted of the conductive silicone rubber electrode 1 containing relatively inexpensive conductive carbon particles, and silver may be used only for the silver coating layer 2. Thus, the amount of silver used can be reduced, so that the manufacturing cost can be kept low.

The bioelectrode of the present invention can be suitably used, for example, to sense an electric signal from a living body, to convey electrical stimulation to the living body, or to perform both operations.

Figure 2:
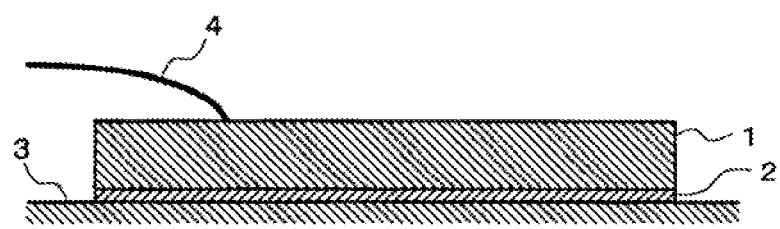
FIG. 2 is a view schematically explaining an example of a use of the bioelectrode of the present invention.

For example, as illustrated in FIG. 2, the conductive silicone rubber electrode 1 is connected to a measuring device via a signal transmission member 4 such as wiring, and the surface of the silver coating layer 2 is brought into contact with a living body 3, so that an electric signal from the living body 3 can be measured by the measuring device.

It is particularly preferable to use the bioelectrode of the present invention as an electric signal to measure an electrocardiogram. The bioelectrode of the present invention can be suitably used, for example, for medical measuring devices, wearable measuring devices, health monitoring devices, and the like.

Hereinafter, the bioelectrode of the present invention will be described in more detail.

The conductive silicone rubber electrode 1 is formed by using conductive carbon particles in rubber. The conductive silicone rubber electrode 1 forms a main body of the bioelectrode, and the shape of the conductive silicone rubber electrode 1 gives the entire shape of the bioelectrode.

As the rubber used in the conductive silicone rubber electrode 1, silicone rubber is selected from the viewpoint of imparting high adhesion between the conductive silicone rubber electrode 1 and the silver coating layer 2.

When rubber other than silicone rubber, such as ethylene-propylene-diene ternary copolymer rubber (abbreviated as EPDM), nitrile rubber, or urethane rubber, is selected, silver paste forming the silver coating layer 2 and including the silver powder and silicone rubber is not cured, and it is impossible to form a bioelectrode having a two-layer configuration formed by the conductive silicone rubber electrode 1 and the silver coating layer 2 (Comparative Examples 1 to 3). Thus, the conductive silicone rubber electrode 1 according to the present invention has to be formed of silicone rubber.

The conductive carbon particles to be used in the conductive silicone rubber electrode 1 are not particularly limited as long as they can impart conductivity to the silicone rubber described above, and, for example, carbon black, graphite and the like are preferable. As the carbon black, Ketjen black, acetylene black and the like can be preferably used, and among them, Ketjen black and the like having relatively high conductivity are particularly preferable.

Although an average particle diameter of the conductive carbon particles is not particularly limited, for example, the average particle diameter is preferably in a range of 0.1 μm to 100 μm, and more preferably in a range of 1 μm to 30 μm. The average particle diameter is an average diameter measured from an electron micrograph and calculated by arithmetic mean.

The amount of the conductive carbon particles added to the conductive silicone rubber electrode 1 can be appropriately set within a range in which conductivity can be imparted, and the amount is in a range of, for example, 10% by weight to 70% by weight, and preferably in a range of 20% by weight to 50% by weight.

The silver coating layer 2 contains silver powder and silicone rubber. The silver coating layer 2 is electrically connected to the conductive silicone rubber electrode 1.

When silicone rubber is used in the silver coating layer 2, the silicone rubber serves as a binder to hold the silver coating layer 2 with respect to the conductive silicone rubber electrode 1 with high adhesion, so that peeling can be prevented. The adhesion also contributes to stabilization of electrical connection between the silver coating layer 2 and the silicone rubber electrode 1. As a result of the above, the contact impedance with a living body can be suitably reduced.

As the silicone rubber, an organosilicon polymer having a siloxane bond (—Si—O—) as a main chain and having a group, such as a methyl group, a phenyl group, a vinyl group, or hydrogen as a side chain can be preferably used.

As the silver powder, at least one of agglomerated silver powder and flake-form silver powder is used. A mixture of the agglomerated silver powder and the flake-form silver powder may be used, and only one of the agglomerated silver powder and the flake-form silver powder may be used. In the present invention, a mixture of the agglomerated silver powder and the flake-form silver powder is preferably used.

Furthermore, granular silver powder which is neither agglomerated silver powder nor flake-form silver powder may be used in combination with the above described silver powder.

The flake-form silver powder means powder having a squamous shape, and examples thereof include "327077" manufactured by Sigma-Aldrich and "FA-D-3" manufactured by Dowa Mining Co., Ltd.

The agglomerated silver powder means powder in which a plurality of particulate primary particles are agglomerated three-dimensionally, and examples thereof include "G-35" manufactured by Dowa Mining Co., Ltd.

Although an average particle diameter of the silver powder is not particularly limited, for example, in the case of the agglomerated silver powder, the average particle diameter is preferably in a range of 4 μm to 8 μm, and in the case of the flake-form silver powder, the average particle diameter is preferably in a range of 5 μm to 15 μm.

The average particle diameter is an average diameter measured from an electron micrograph and calculated by arithmetic mean.

The total amount of the silver powder to be added in the silver coating layer 2 can be suitably set within a range that can impart conductivity, but it is preferably in a range of 50 phr by weight to 500 phr by weight, for example, based on 100 phr by weight of silicone rubber, and particularly preferably in a range of 100 phr by weight to 300 phr by weight.

The silver coating layer 2 is formed to have a thickness of 18 μm to 80 μm. In particular, the thickness is preferably in a range of 30 μm to 60 μm. Consequently, the adhesion of the silver coating layer 2 to the conductive silicone rubber electrode 1 can be further increased, so that peeling of the silver coating layer 2 can be further prevented, and, at the same time, the contact impedance can be reduced.

The bioelectrode of the present invention can be used by connecting the conductive silicone rubber electrode 1 to a measuring device via the signal transmission member 4 such as wiring. A configuration example of the signal transmission member 4 will be described in more detail with reference to FIGS. 3A and B.

Figure 3A:
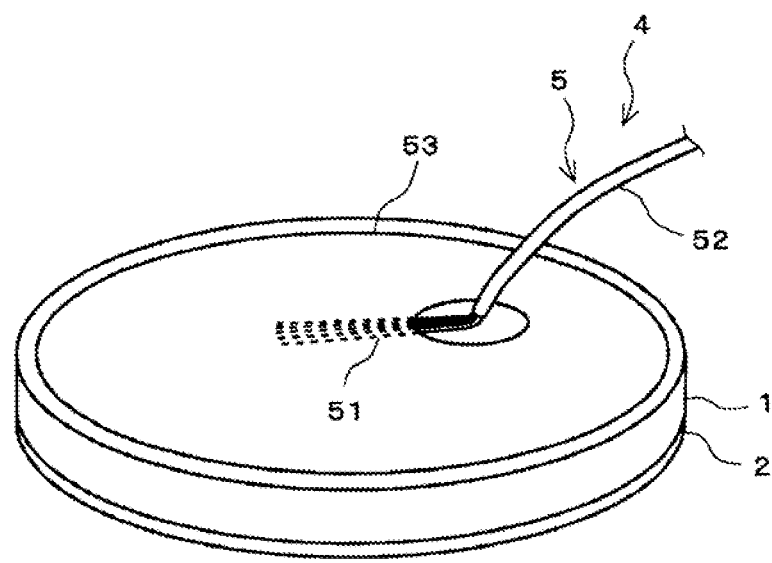
FIG. 3A and FIG. 3B are views schematically explaining an example of a signal transmission member.

First, in the example of FIG. 3A, the signal transmission member 4 is constituted of a coated wire 5. The coated wire 5 is constituted of a metal core wire 51 and a resin coating material 52 covering the core wire 51. The coated wire 5 is provided to bring the core wire 51 exposed from the coating material 52 into contact with an upper surface (a surface opposite to the silver coating layer 2) of the conductive silicone rubber electrode 1. Reference numeral 53 denotes an adhesive tape for fixing the core wire 51 on the upper surface of the conductive silicone rubber electrode 1.

Figure 3B:
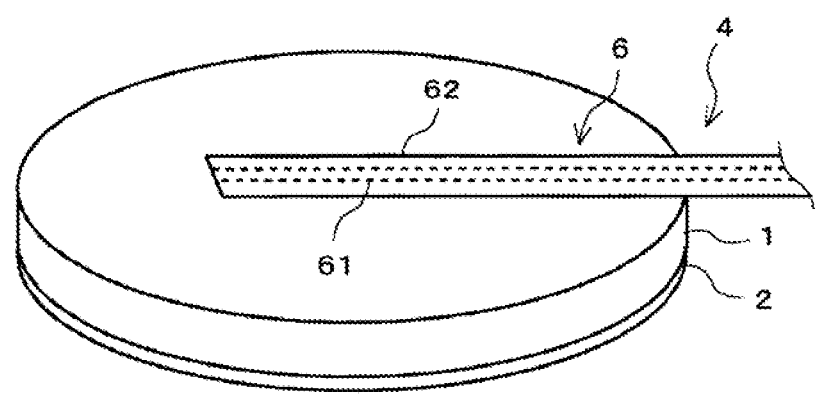

Next, in the example of FIG. 3B, the signal transmission member 4 is constituted of FPC (a flexible printed wiring board (also referred to as a flexible printed circuits)) 6. The FPC 6 is constituted of a resin base film 62 and a metal conductor foil (also referred to as an electrode part) 61 adhering onto the base film 62. The FPC 6 is provided to bring a surface on which the conductor foil 61 is provided into contact with the upper surface of the conductive silicone rubber electrode 1. The surface of the conductor foil 61, that is, the contact surface with respect to the conductive silicone rubber electrode 1 can be preferably formed of copper, gold plated on copper, or the like.

Although the upper surface of the conductive silicone rubber electrode 1 is not brought into direct contact with a mounting portion of a living body, when the coated wire 5 which is the signal transmission member 4 protrudes from the upper surface as illustrated in FIG. 3A, due to deformation of the conductive silicone rubber electrode 1 formed of rubber, an uneven load is applied to the silver coating layer 2 to be brought into direct contact with the mounting portion, and an uneven feel may be provided in the mounting portion. On the other hand, when the signal transmission member 4 is constituted of the FPC 6 as illustrated in FIG. 3B, since the FPC 6 is flush with the upper surface of the conductive silicone rubber electrode 1 and hardly protrudes, an uneven feel is less likely to be provided in the mounting portion even if it remained mounted for a long time, and discomfort can be reduced. Furthermore, when the signal transmission member 4 is constituted of the FPC 6, weight and size reduction can be achieved.

Figure 4:
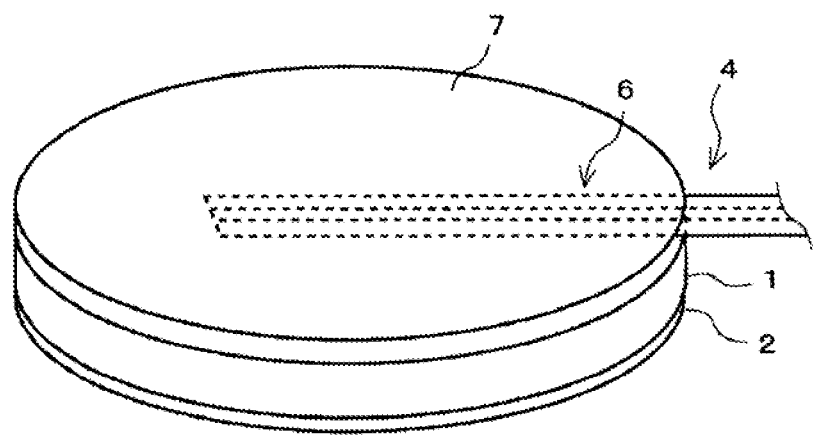
FIG. 4 is a view schematically explaining an example in which an insulating layer is provided in the bioelectrode.

In the bioelectrode, since the upper surface of the conductive silicone rubber electrode 1 is not in contact with the living body, it is also preferable to provide an insulating layer 7 on this upper surface as illustrated in FIG. 4. The insulating layer 7 is preferably formed of insulating rubber.

When the insulating layer 7 is provided, it is preferable that the signal transmission member 4 is constituted of the FPC 6 as illustrated. Since the FPC 6 is flush with the upper surface of the conductive silicone rubber electrode 1 and hardly protrudes, the insulating layer 7 can be stably held, and the conductive silicone rubber electrode 1 can be prevented from being curved.

Method of Manufacturing Bioelectrode

Next, a method of manufacturing the bioelectrode according to the first embodiment of the present invention will be described.

In the method of manufacturing the bioelectrode according to the first embodiment of the present invention, a conductive silicone rubber electrode obtained by using conductive carbon particles in silicone rubber is first provided, silver paste containing silver powder and silicone rubber is then applied on the conductive silicone rubber electrode, and the silver paste is then cured to form a silver coating layer such that the silver coating layer has a thickness of 18 µm to 80 µm. Consequently, the bioelectrode of the present invention described above can be suitably manufactured.

The conductive silicone rubber constituting the conductive silicone rubber electrode can be obtained, for example, by using conductive carbon particles in uncrosslinked rubber, kneading the mixture to obtain a dough, then molding the dough by injection molding, compression molding or the like, and crosslinking the molded article. In a particularly preferred embodiment, the conductive silicone rubber is obtained by primarily crosslinking the dough by press crosslinking and further subjecting the dough to secondary crosslinking. A crosslinking agent, a crosslinking accelerator, and other commonly known rubber filler can be appropriately used in the dough. As the conductive silicone rubber, a commercial product may be used. The conductive silicone rubber can be molded into a predetermined electrode shape and used.

The silver paste applied on the conductive silicone rubber electrode can be prepared by mixing the silver powder and silicone rubber. As such silver paste, those described below may be particularly preferably used.

As described above, as the silicone rubber, an organosilicon polymer having a siloxane bond (—Si—O—) as a main chain and having a group, such as a methyl group, a phenyl group, a vinyl group, or hydrogen as a side chain can be preferably used. Silicone rubber can be roughly divided into an addition reaction type and a condensation reaction type depending on difference in curing method. The addition reaction type silicone rubber is silicone rubber cured by an addition reaction, and examples thereof include silicone rubber having hydrogen or a vinyl group as a side chain. On the other hand, the condensation reaction type silicone rubber is silicone rubber cured by a condensation reaction, and examples thereof include silicone rubber having an —OH group at a terminal end. Among them, the addition reaction type silicone rubber is particularly preferred, whereby the adhesion of the silver coating layer can be more suitably retained. The addition reaction type silicone rubber is commercially available as two-component type silicone rubber with using a curing agent, and examples thereof include "KE1031" and "KE106" manufactured by Shin-Etsu Chemical Co., Ltd. When silver paste is prepared using the two-component type silicone rubber, it is preferable that silver powder is mixed before a curing agent is used, and the curing agent is used immediately before application and mixed to obtain the silver paste.

The amount of the silver powder to be added in the silver paste can be suitably set within a range that can impart conductivity to the silver coating layer 2 and is preferably set such that the total amount of the silver powder to be added in the silver coating layer 2 is in the above range.

Examples of the method of applying the silver paste to the surface of the conductive silicone rubber electrode 1 include application methods such as immersion, spraying, roll coater, flow coater, ink jet, and screen printing, but the present invention is not limited to these methods.

Although the application thickness of (thickness before curing) of the silver paste to the conductive silicone rubber electrode 1 is not particularly limited, the application thickness is preferably in a range of 25 µm to 200 µm, and more preferably in a range of 35 µm to 100 µm. Consequently, the adhesion of the silver coating layer 2 to the conductive silicone rubber electrode 1 can be further increased, so that peeling of the silver coating layer 2 can be further prevented, and, at the same time, the contact impedance can be reduced.

When the silver paste is cured, heating is preferably performed. The heating temperature and the heating time can be appropriately set so as to be able to cure silicone rubber. For example, the heating temperature is preferably in a range of 50° C. to 200° C., and the heating time is preferably in a range of 10 minutes to 10 hours.

As described with reference to FIG. 3B, it is preferable that the signal transmission member connected to the conductive silicone rubber electrode 1 is constituted of the FPC 6. As a method of fixing the FPC 6 to the conductive silicone rubber electrode 1, a method of directly forming the conductive silicone rubber electrode 1 on the FPC 6 can be preferably exemplified. At that time, on a surface of the FPC 6 to be brought into contact with the conductive silicone rubber electrode 1, on the base film 62 not provided with the conductor foil 61, in order to increase the adhesion to the conductive silicone rubber electrode 1, the base film 62 is preferably coated with an adhesive such as a primer beforehand. Examples of the method of coating the adhesive on the base film 62 include screen printing, but the present invention is not limited to this.

As described with reference to FIG. 4, it is preferable that the insulating layer 7 is provided on the upper surface of the conductive silicone rubber electrode 1. The method of stacking the insulating layer 7 on the upper surface of the conductive silicone rubber electrode 1 is not particularly limited. As a preferred method, there may be mentioned a method in which the insulating layer 7 is first formed, the signal transmission member 4 is then placed on the insulating layer 7, and the conductive silicone rubber electrode 1 is then formed on the insulating layer 7 and the signal transmission member 4 placed on the insulating layer 7.

2. Second Embodiment

Bioelectrode

A bioelectrode of the second embodiment has, on a conductive silicone rubber electrode 1 obtained by using conductive carbon particles in silicone rubber, a silver coating layer 2 formed of at least one of agglomerated silver powder and flake-like silver powder and silicone rubber, and the silver coating layer 2 has electrical conductivity (electron conductivity) and ionic conductivity.

The second embodiment has the same technical features as those of the first embodiment in the following points.

The bioelectrode of the present invention includes the silver coating layer 2 on a surface in contact with a living body and therefore can achieve the electrical conduction by silver, and since this bioelectrode is a rubber flexible electrode, the bioelectrode has good adhesion to the living body and does not give an unpleasant feeling even if the bioelectrode firmly adheres for a long time.

When the silver coating layer 2 contains silicone rubber as a binder together with the silver powder, high adhesion to the conductive silicone rubber electrode 1 is exhibited, and peeling is prevented, so that contact impedance with a living body can be suitably reduced. Thus, effects can be obtained that biological information can be stably measured and it is suitable for repeated use.

Since there is no need to use a gel or the like at this time, stable measurement can be achieved even under dry conditions, and the method of use is simple.

In the second embodiment, since the portions having the same reference numerals as the bioelectrode described in the first embodiment indicate portions having the same configuration, the explanation of the first embodiment is basically applied, and the explanation thereof will be omitted here. However, the thickness of the silver coating layer 2 is not limited to this. In the second embodiment, although the thickness of the silver coating layer 2 is preferably in a range of 18 µm to 80 µm, the present invention is not limited to this.

In the second embodiment, the silver coating layer 2 has electrical conductivity and ionic conductivity.

The silver coating layer 2 contains the silver powder, so that the electrical conductivity of the silver coating layer 2 is imparted.

The ionic conductivity of the silver coating layer 2 can be imparted by causing ions to exist between particles of the silver powder.

Although the method of causing ions to exist is not particularly limited, a method of immersing the silver coating layer 2 in a solution prepared by dissolving an inorganic salt can be exemplified.

Preferred examples of the inorganic salt include chloride salt, sulfate, and carbonate, and these can be used singly or in combination.

Examples of the chloride salt include sodium chloride, potassium chloride, lithium chloride, calcium chloride, and magnesium chloride.

Examples of the sulfate include sodium sulfate, potassium sulfate, lithium sulfate, calcium sulfate, and magnesium sulfate.

Examples of the carbonate include sodium carbonate, potassium carbonate, lithium carbonate, calcium carbonate, and magnesium carbonate.

Among the above inorganic salts, chloride salts of alkali metals such as sodium chloride, potassium chloride, and lithium chloride are particularly preferable from the viewpoints of solubility in a solvent, ion mobility and the like.

The solvent is not particularly limited as long as it dissolves the inorganic salt. For example, a solvent alone including water, a ketone such as acetone, and an alcohol such as ethanol or a mixed solvent in combination of two or more of these can be used. In particular, water, ethanol, and a mixture of water and ethanol can be preferably used.

The concentration of the solution prepared by dissolving the inorganic salt is not particularly limited and can be appropriately set to a concentration capable of imparting the ionic conductivity to the silver coating layer 2.

For example, when an aqueous sodium chloride solution prepared by dissolving sodium chloride in water is used, ions dissociated into chloride ions and sodium ions in the aqueous solution are taken into the silver coating layer 2 by immersion and dispersed between the particles of the silver powder.

The bioelectrode of the present invention in which the silver coating layer 2 has the ionic conductivity can stably exhibit conductivity even when an external force such as bending is applied to the bioelectrode. As the external force such as bending, for example, an action such as washing can be considered.

Usually, when an external force is applied to a bioelectrode by an action such as washing, in the bioelectrode having only electrical conductivity by silver powder, a space tends to be formed between particles of the silver powder by the external force, so that the conductivity tends to degrade.

However, when the silver coating layer 2 has the ionic conductivity in addition to the electrical conductivity, the conductivity can be prevented from degrading. That is, in the bioelectrode in which the silver coating layer 2 has the ionic conductivity, even when an external force accompanying an action such as washing is applied to the bioelectrode, the conductivity can be retained since the existence of ions in a space between silver particles can retain conductivity, so that the conductivity can be stably exhibited. Consequently, in use, the problem that a target signal cannot be measured due to noise mixed in a measurement signal can be avoided.

In the second embodiment, as in the first embodiment, the conductive silicone rubber electrode 1 can be used by connecting the conductive silicone rubber electrode 1 to a measuring device via the signal transmission member 4 such as wiring. Furthermore, in the second embodiment, as in the first embodiment, an insulating layer 7 can be provided. Since these configuration examples indicate that they have the same configuration as the same reference numerals in the first embodiment, the explanation of the first embodiment is basically applied, and the explanation thereof will be omitted here.

Method of Manufacturing Bioelectrode

Next, a method of manufacturing the bioelectrode according to the second embodiment of the present invention will be described.

In the method of manufacturing the bioelectrode according to the second embodiment of the present invention, the conductive silicone rubber electrode 1 obtained by using conductive carbon particles in silicone rubber is first provided, silver paste containing at least one of agglomerated silver powder and flake-like silver powder and silicone rubber is then applied on the conductive silicone rubber electrode 1, and cured to form the silver coating layer 2 having electrical conductivity, and the ionic conductivity is then imparted by causing ions to exist between particles of the silver powder of the silver coating layer 2. Consequently, the bioelectrode of the present invention described above can be suitably manufactured.

In the second embodiment, since the portions having the same reference numerals as the bioelectrode described in the first embodiment indicate portions having the same configuration, the explanation of the first embodiment is basically applied, and the explanation of the manufacturing method will be omitted here. However, the method of forming the silver coating layer 2 is not limited to this. In the second embodiment, although it is preferable that the silver coating layer 2 is applied to have a thickness of 18 μm to 80 μm, the present invention is not limited to this.

In the method of manufacturing the bioelectrode according to the second embodiment, after the silver coating layer 2 having electrical conductivity by silver powder is formed, the ionic conductivity is then imparted by causing ions to exist between particles of the silver powder of the silver coating layer 2.

The ionic conductivity can be imparted by causing ions to exist between the particles of the silver powder of the silver coating layer 2. Although the method of causing ions to exist is not limited, the method of immersing the silver coating layer 2 in a solution prepared by dissolving the above-described inorganic salt in a solvent can be preferably used. The concentration of the solution is not particularly limited. In addition, the immersion time is not particularly limited, and, for example, may be 10 minutes to 5 hours depending on the solution concentration.

According to experiments by the present inventor, it has been found that even if an inorganic salt (for example, sodium chloride) is directly added to the silver paste before forming the silver coating layer 2, the effect of imparting the ionic conductivity cannot be suitably obtained. The reason is that uniform ionic conductivity cannot be obtained because the inorganic salt does not dissolve and the viscosity of the silver paste increases to make it difficult to apply the silver paste. According to further experiments by the present inventor, it has also been found that even if a solution prepared by dissolving an inorganic salt is added to silver paste, the effect of imparting the ionic conductivity cannot be suitably obtained. This is because separation of water and inhibition of curing are caused, and ideal conductivity cannot be obtained. Thus, in the present invention, as the method of imparting the ionic conductivity, it is preferable to immerse the surface of the silver coating layer 2 in the solution prepared by dissolving an inorganic salt.

Also in the second embodiment, as in the first embodiment, the signal transmission member connected to the conductive silicone rubber electrode 1 can be constituted of the FPC 6. In addition, as in the first embodiment, the insulating layer 7 may be provided on the upper surface of the conductive silicone rubber electrode 1. The explanation of the first embodiment can be applied to these forming methods, and the explanation thereof will be omitted here.

EXAMPLES

Hereinafter, examples of the present invention will be described. However, the present invention is not limited to these examples.

I. Test 1 (Illustration of First Embodiment)

Example 1

1. Production of Bioelectrode 1
(1) Production of Conductive Silicone Rubber Electrode After the following formulation components were kneaded by a kneader for 10 minutes, a dough (containing 6% by volume of carbon black) further kneaded with a roll for 3 minutes was press-crosslinked (primary crosslinking) at 180° C. for 4 minutes and then subjected to secondary crosslinking at 230° C. for 5 hours to obtain a sheet formed of conductive silicone rubber and having a thickness of 0.5 mm.

Electrode Body: Formulation Components

| | |
|---|---|
| Conductive silicone rubber ("KE-3801M-U") manufactured by Shin-Etsu Chemical Co., Ltd.; containing carbon black) | 100 phr by weight |
| Crosslinking agent ("C-8A" manufactured by Shin-Etsu Chemical Co., Ltd.; containing 80% by weight of 2,5-dimethyl-2,5-bis(t-butylperoxy)hexane) | 1.0 phr by weight |

(2) Preparation of Silver Paste

With 100 phr by weight of silicone rubber ("KE-1031" manufactured by Shin-Etsu Chemical Co., Ltd.), 100 phr by weight of the following silver powder A-1 and 100 phr by weight of the following silver powder B-1 were mixed and stirred to prepare silver paste.

Silver powder A-1 ("327093" manufactured by Sigma-Aldrich Co., particulate shape, the average particle diameter being 5 μm to 8 μm)

Silver powder B-1 ("327077" manufactured by Sigma-Aldrich Co., flake shape, the average particle diameter being 10 μm)

(3) Formation of Silver Coating Layer and Production of Bioelectrode

The prepared silver paste was uniformly applied with a thickness of 50 μm to one side surface of a sheet-like conductive silicone rubber electrode, and the coated sheet-like conductive silicone rubber electrode was placed in an oven set at 120° C. for 2 hours so that the silver paste was cured, and thus a silver coating layer was formed on the conductive silicone rubber electrode.

In the manner described above, a bioelectrode 1 including the sheet-like conductive silicone rubber electrode having the silver coating layer formed thereon was obtained.

2. Bioelectrode 2

A bioelectrode 2 was produced in the same manner as the bioelectrode 1, except that in the bioelectrode 1, the silver powder A-1 was replaced with the following silver powder C-1 and the silver powder B-1 was replaced with the following silver powder B-2.

Silver powder C-1 ("G-35" manufactured by Dowa Mining Co., Ltd., agglomerated shape, the average particle diameter being 5.9 μm)

Silver powder B-2 ("FA-D-3" manufactured by Dowa Mining Co., Ltd., flake shape, the average particle diameter being 6.9 μm)

3. Production of Bioelectrode 3

A bioelectrode 3 was produced in the same manner as the bioelectrode 1, except that in the bioelectrode 1, "(2) Formation of Silver Coating Layer" was omitted.

4. Production of Bioelectrode 4

A bioelectrode 4 was produced in the same manner as the bioelectrode 2, except that in the bioelectrode 2, "(1) Production of Conductive Silicone Rubber Electrode" was omitted and silver paste was uniformly applied with a thickness of 50 μm on a fluorocarbon resin film.

5. Production of Bioelectrode 5

A bioelectrode 5 was produced in the same manner as the bioelectrode 1, except that in the bioelectrode 1, among silver powders, only the following silver powder A-2 was replaced with 200 phr by weight of silver powder.

Silver powder A-2 ("AGE08PB" manufactured by Kojundo Chemical Laboratory Co., Ltd., particulate shape, the average particle diameter being 1 μm)

Physical Property Evaluation

Each bioelectrode produced as described above was punched into a size of 100 mm×100 mm to produce a bioelectrode for surface resistance measurement, and the surface resistance was measured by a four terminal method ("Loresta" manufactured by Mitsubishi Chemical Analytech Co., Ltd.).

In addition, the thickness of the silver coating layer was measured from a microscopic image of the section of the bioelectrode.

The measurement results are listed in Table 1.

Noise Evaluation

The bioelectrode 1 and the bioelectrode 5 were punched to be φ 19 mm and have a thickness of 0.5 mm to produce the bioelectrode 1 and the bioelectrode 5 for noise evaluation, and a circuit connecting these bioelectrodes to a human body and an electrocardiogram measurement device is formed. After that, an electrocardiogram of an adult male was measured, and the waveform displayed by an electrocardiogram meter was recorded. The results are illustrated in FIGS. 5A and 5B.

Furthermore, as a reference, conductive paste was applied on a human body, and the waveform displayed by the electrocardiogram meter was recorded in the same manner as the bioelectrode 1 and the bioelectrode 5, using a metal bioelectrode formed of silver as a commercial product. The results are illustrated in FIGS. 5A and 5B.

Figure 5A:
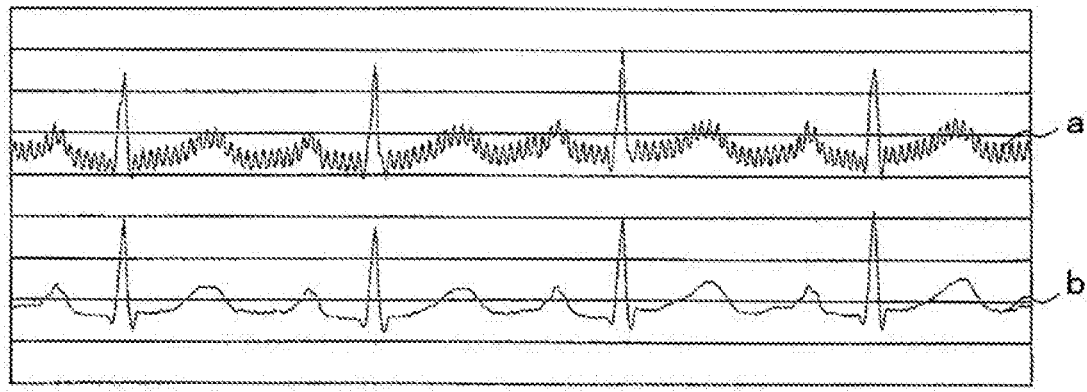
FIG. 5A and FIG. 5B are views illustrating an electrocardiogram waveform of an adult male measured using the bioelectrode.

In FIG. 5A, an upper electrocardiogram waveform a is an electrocardiogram waveform measured using the bioelectrode 5, and a lower electrocardiogram waveform b is an electrocardiogram waveform measured using a commercial product (metal bioelectrode formed of silver).

Figure 5B:
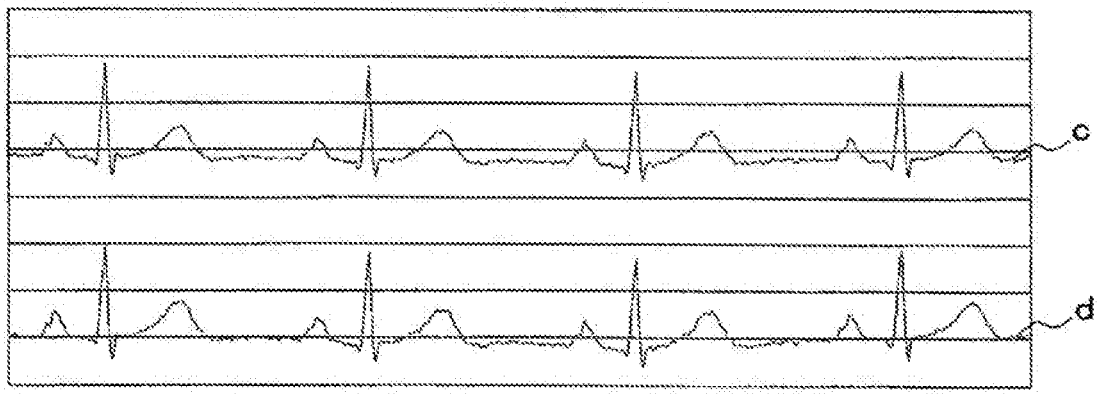

In FIG. 5B, an upper electrocardiogram waveform c is an electrocardiogram waveform measured using the bioelectrode 1, and a lower electrocardiogram waveform d is an electrocardiogram waveform measured using a commercial product (metal bioelectrode formed of silver).

As illustrated in the waveform a in FIG. 5A, since the surface resistance of the bioelectrode 5 exceeds 1Ω, the measured electrocardiogram waveform is very noisy.

In contrast, as illustrated in the waveform c in FIG. 5B, since the surface resistance of the bioelectrode 1 is not higher than 1Ω, there is very little noise.

This result indicates that a stable electrocardiogram waveform comparable to that of a commercial product (metal bioelectrode formed of silver) used as a reference has been measured.

For the bioelectrode 2 and the bioelectrode 3, the noise evaluation was performed by recording electrocardiogram waveforms similarly to the bioelectrode 1 and the bioelectrode 5. Although the resulting electrocardiogram waveforms are omitted, in the bioelectrode 2, there was very little noise similarly to the bioelectrode 1, and in the bioelectrode 3, there was a lot of noise similarly to the bioelectrode 5.

From the above results, it is evaluated that the bioelectrode of the present invention satisfies sufficient performance as a bioelectrode if the surface resistance is not higher than 1Ω. That is, it has been demonstrated that the contact impedance is low.

Performance Evaluation

As described above, experiments by the present inventor have confirmed that as a bioelectrode, when the surface resistance exceeds 1Ω, noise increases when the bioelectrode is used for electrocardiogram measurement, and therefore, in the present experiment, each bioelectrode is evaluated according to the following evaluation criteria, and the results are listed in Table 1.

Evaluation Criteria

○: The surface resistance is not higher than 1Ω.
x: The surface resistance exceeds 1Ω.

TABLE 1

| Bioelectrode No. | Presence (P)/ Absence (A) of conductive rubber electrode | Type of silver powder | | Surface resistance (Ω) | Thickness (μm) | Evaluation | Notes |
| --- | --- | --- | --- | --- | --- | --- | --- |
| 1 | P | A-1 | B-1 | 0.60 | 18 | ○ | Example |
| 2 | P | C-1 | B-2 | 0.11 | 23 | ○ | Example |
| 3 | P | — | — | 6-8 | — | X | Comparison |
| 4 | A | C-1 | B-2 | unmeasurable | 58 | X | Comparison |
| 5 | P | A-2 | — | 6-8 | 18 | X | Comparison |

Evaluation

As listed in Table 1, when the bioelectrode was constituted only by the conductive silicone rubber electrode (bioelectrode 3), since the surface resistance was as high as 6Ω to 8Ω, the performance as an electrode was insufficient.

Furthermore, when the bioelectrode was constituted only by the silver coating layer (bioelectrode 4), the conductivity was not developed, and the surface resistance could not be measured; therefore, the bioelectrode did not function as an electrode.

Furthermore, in a bioelectrode including a conductive silicone rubber electrode and a silver coating layer provided on one side surface of the conductive silicone rubber electrode, when at least agglomerated silver powder (C-1) or a flake-like silver powder (B-1, B-2) was used as silver powder to be used in the silver coating layer, the surface resistance was 0.06Ω or 0.01Ω (bioelectrode 1, bioelectrode 2).

In contrast, when only particulate silver powder was used (bioelectrode 5), the surface resistance was as high as 6Ω to 8Ω, and the performance as an electrode was insufficient.

Accordingly, it can be seen that the bioelectrode of the present invention includes the conductive silicone rubber electrode and the silver coating layer and must contain at least agglomerated silver powder or flake-like silver powder as the silver powder of the silver coating layer.

Example 2

Evaluation in the Case of Changing Ratio of Silver Powder to Silver Paste

A bioelectrode was produced in the same manner as the bioelectrode 2, except that in the bioelectrode 2, the amounts of the silver powder C-1 and the silver powder B-2 to be added were changed as indicated in bioelectrodes 6 to 15 listed in Table 2, and the bioelectrodes were evaluated in the same manner as the bioelectrode 2. The results are listed in Table 2.

TABLE 2

| Bio-electrode No. | Amount of silver powder to be added (phr by weight) | | Surface resistance, ($\Omega$) | Thickness ($\mu$m) | Evaluation | Notes |
|---|---|---|---|---|---|---|
| | C-1 | B-2 | | | | |
| 6 | 0 | 200 | 0.8 | 27 | ○ | Example |
| 7 | 20 | 180 | 0.10 | 20 | ○ | Example |
| 8 | 50 | 150 | 0.11 | 28 | ○ | Example |
| 9 | 60 | 140 | 0.11 | 36 | ○ | Example |
| 10 | 80 | 120 | 0.10 | 33 | ○ | Example |
| 11 | 120 | 80 | 0.09 | 40 | ○ | Example |
| 12 | 140 | 60 | 0.13 | 36 | ○ | Example |
| 13 | 150 | 50 | 0.11 | 40 | ○ | Example |
| 14 | 180 | 20 | 0.33 | 27 | ○ | Example |
| 15 | 200 | 0 | 0.28 | 28 | ○ | Example |

Evaluation

Table 2 indicates that when agglomerated silver powder (C-1) or flake-like silver powder (B-2) is contained, one type of silver powder may be used.

Example 3

Evaluation in the Case of Changing Thickness of Silver Coating Layer

Bioelectrodes were produced in the same manner as the bioelectrode 2, except that in the bioelectrode 2, silver paste was uniformly applied with different thicknesses such that the thickness of the silver coating layer listed in Table 3 was obtained, and bioelectrodes 16 to 25 were produced, and the bioelectrodes were evaluated in the same manner as the bioelectrode 2. The results are listed in Table 3.

TABLE 3

| Bio-electrode No. | Thickness ($\mu$m) | Surface resistance ($\Omega$) | Evaluation | Notes |
|---|---|---|---|---|
| 16 | 5 | 5.20 | X | Comparison |
| 17 | 14 | 2.50 | X | Comparison |
| 18 | 21 | 0.54 | ○ | Example |
| 19 | 22 | 0.15 | ○ | Example |
| 20 | 43 | 0.04 | ○ | Example |
| 21 | 63 | 0.03 | ○ | Example |
| 22 | 120 | unmeasurable | X | Comparison |
| 23 | 139 | unmeasurable | X | Comparison |
| 24 | 157 | unmeasurable | X | Comparison |
| 25 | 221 | unmeasurable | X | Comparison |

Evaluation

As apparent from Table 3, when the thickness of the silver coating layer was not larger than 18 $\mu$m, the surface resistance was large, and the performance as an electrode was insufficient. If such an electrode was used for electrocardiogram measurement or the like, there was a lot of noise, so that the measurement became unstable.

When the thickness of the silver coating layer was not smaller than 120 $\mu$m, the surface resistance could not be measured. Thus, even if the thickness was too thick, the bioelectrode was not suitable because it did not function as an electrode.

Comparative Example 1

An attempt was made to produce a bioelectrode in the same manner as the bioelectrode 1, except that in the bioelectrode 1, <Electrode Body: Formulation Components> in the conductive silicone rubber electrode was replaced with the following composition and the crosslinking conditions were changed as follows.

Electrode Body: Formulation Components

| | |
|---|---|
| EPDM ("EPT3070" manufactured by Mitsui Chemicals, Inc.) | 100 phr by weight |
| Ketjen black ("EC600JD" manufactured by Lion Corporation) | 30 phr by weight |
| Stearic acid | 1 phr by weight |
| Plasticizer ("Diana Process Oil PW-380" manufactured by Idemitsu Kosan Co., Ltd. | 120 phr by weight |
| Zinc oxide | 5 phr by weight |
| Antioxidant ("Nocrac White" manufactured by Ouchi Shinko Chemical Industrial Co., Ltd.) | 2 phr by weight |
| Sulfur | 2 phr by weight |
| Crosslinking accelerator ("Nocceler CZ" manufactured by Ouchi Shinko Chemical Industrial Co., Ltd.) | 2 phr by weight |

Crosslinking Conditions

Primary crosslinking: press crosslinking at 180° C. for 10 minutes

Secondary crosslinking: at 150° C. for 15 hours

Evaluation

Silver paste applied on an electrode body formed of the conductive EPDM rubber was not cured, so that a silver coating layer could not be formed.

Comparative Example 2

An attempt was made to produce a bioelectrode in the same manner as the bioelectrode 1, except that in the bioelectrode 1, <Electrode Body: Formulation Components> in the conductive silicone rubber electrode was replaced with the following composition and the crosslinking conditions were changed as follows.

Electrode Body: Formulation Components

| | |
|---|---|
| Medium-nitrile NBR ("N-237" manufactured by JSR Corporation) | 100 phr by weight |
| Acetylene black | 40 phr by weight |
| SRF carbon | 5 phr by weight |
| Graphite AO | 35 phr by weight |
| Zinc flower (zinc oxide) | 5 phr by weight |
| Stearic acid | 1.5 phr by weight |
| Antioxidant (RD) | 2 phr by weight |
| Dioctyl sebacate | 7 phr by weight |
| Sulfur | 0.8 phr by weight |
| Vulcanizing accelerator (TT) | 2.5 phr by weight |
| Vulcanizing accelerator (CZ) | 3 phr by weight |

Crosslinking Condition
Press crosslinking at 155° C. for 20 minutes
Evaluation
Silver paste applied on an electrode body formed of the conductive NBR rubber was not cured, so that a silver coating layer could not be formed.

Comparative Example 3

An attempt was made to produce a bioelectrode in the same manner as the bioelectrode 1, except that in the bioelectrode 1, <Electrode Body: Formulation Components> in the conductive silicone rubber electrode was replaced with the following composition and the crosslinking conditions were changed as follows.
Electrode Body: Formulation Components

| | |
|---|---|
| Millable urethane rubber ("ADIPRENE CM" manufactured by Du Pont); polyether type polyurethane | 100 phr by weight |
| Ketjen black EC (manufactured by Lion Corporation; the surface area being 800 m²/g) | 8 phr by weight |
| Furnace black ("DIABLACK H" manufactured by Mitsubishi Chemical Corporation; the surface area being 85 m²/g) | 15 phr by weight |
| Organic peroxide ("PERCUMYL D40" manufactured by NOF Corporation) | 2 phr by weight |
| Stearic acid ("Lunac S30" manufactured by Kao Corporation) | 0.25 phr by weight |

Crosslinking Conditions
Primary crosslinking: press crosslinking at 160° C. to 180° C. for 7 minutes to 10 minutes
Secondary crosslinking: at 100° C. to 120° C. for 15 hours to 24 hours
Evaluation
Silver paste applied on an electrode body formed of the conductive urethane rubber was not cured, so that a silver coating layer could not be formed.

II. Test 2 (Illustration of Second Embodiment)

1. Production of Bioelectrode 26
(1) Production of Conductive Silicone Rubber Electrode
After the following formulation components were kneaded by a kneader for 10 minutes, a dough (containing 6% by volume of carbon black) further kneaded with a roll for 3 minutes was press-crosslinked (primary crosslinking) at 180° C. for 4 minutes and then subjected to secondary crosslinking at 230° C. for 5 hours to obtain a sheet formed of conductive silicone rubber.
Electrode Body: Formulation Components

| | |
|---|---|
| Conductive silicone rubber ("KE-3801M-U" manufactured by Shin-Etsu Chemical Co., Ltd.; containing carbon black) | 100 phr by weight |
| Crosslinking agent ("C-8A" manufactured by Shin-Etsu Chemical Co., Ltd.; containing 80% by weight of 2,5-dimethyl-2,5-bis(t-butylperoxy)hexane) | 1.0 phr by weight |

(2) Preparation of Silver Paste
With 100 phr by weight of silicone rubber ("KE-106" manufactured by Shin-Etsu Chemical Co., Ltd.), 150 phr by weight of the following silver powder B-2 and 150 phr by weight of the following silver powder C-1 were subjected to centrifugal stirring to prepare silver paste.

Figure 6:
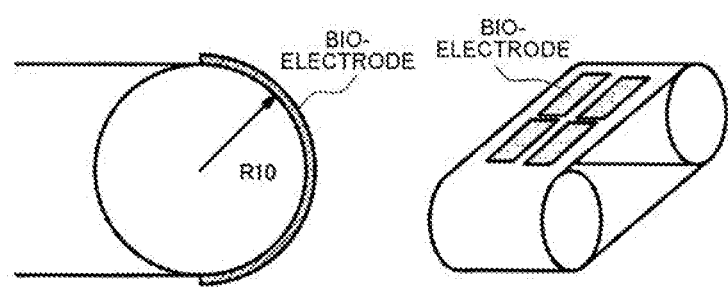
FIG. 6 is a view illustrating an electrocardiogram waveform of an adult male measured using the bioelectrode.
Figure 7:
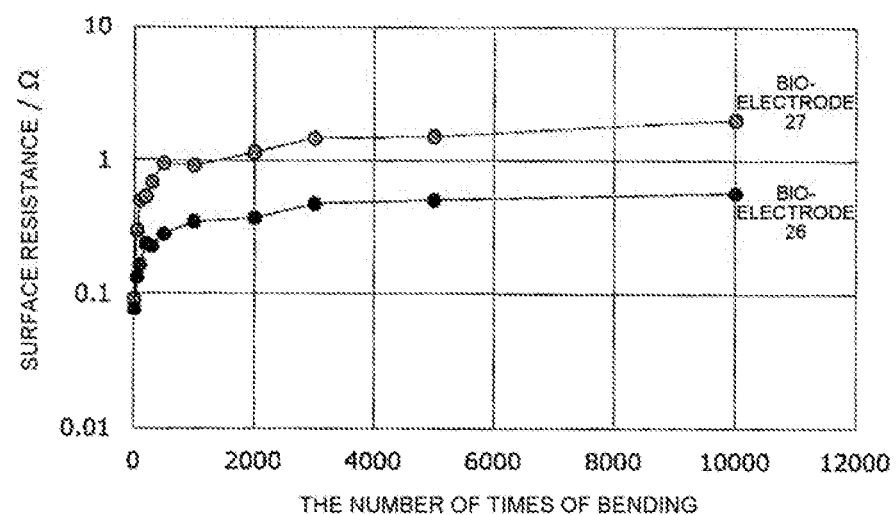
FIG. 7 is a conceptual diagram of a conveyer belt used in Test 2.

Silver powder B-2 ("FA-D-3" manufactured by Dowa Mining Co., Ltd., flake shape, the average particle diameter being 6.9 μm)
Silver powder C-1 ("G-35" manufactured by Dowa Mining Co., Ltd., agglomerated shape, the average particle diameter being 5.9 μm)
(3) Formation of Silver Coating Layer
The prepared silver paste was applied on one side surface of a sheet-like conductive silicone rubber electrode by screen printing and cured at 150° C. for 30 minutes to obtain an electrode sheet in which a silver coating layer was formed on the conductive silicone rubber electrode.
(4) Salt-Adding Treatment and Production of Bioloelectrode
After the silver coating layer was cured, the electrode sheet was immersed in a sodium chloride aqueous solution having a concentration of 1% by weight for 1 hour, taken out, and dried. A bioelectrode 26 was thus obtained.
2. Production of Bioelectrode 27
A bioelectrode 27 was produced in the same manner as the bioelectrode 26, except that in the bioelectrode 26, "(4) Salt-Adding Treatment" was omitted.
Physical Property Evaluation
The bioelectrodes 26 and 27 produced as described above were punched into a size of 100 mm×100 mm, and the surface resistance was measured by a four terminal method ("Loresta" manufactured by Mitsubishi Chemical Analytech Co., Ltd., using a PSP terminal). The results are listed in Table 4.
Noise Evaluation
The bioelectrode 26 and the bioelectrode 27 were punched to be φ 19 mm and have a thickness of 0.5 mm to produce the bioelectrode 26 and the bioelectrode 27 for noise evaluation, and a circuit connecting these bioelectrodes to a human body and an electrocardiogram measurement device was formed. After that, an electrocardiogram of an adult male was measured, and the waveform displayed by an electrocardiogram meter was recorded. The respective results are illustrated in FIG. 6.
Furthermore, as a reference, the waveform displayed by the electrocardiogram meter was recorded in the same manner as the bioelectrode 26 and the bioelectrode 27, using a gel electrode as a commercially available wet electrode. The results are illustrated in FIG. 6.
In FIG. 6, an upper electrocardiogram waveform a is an electrocardiogram waveform measured using the bioelectrode 27, a middle electrocardiogram waveform b is an electrocardiogram waveform measured using the bioelectrode 26, and a lower electrocardiogram waveform c is an electrocardiogram waveform measured using a commercial product (gel electrode).
As illustrated by the waveforms a to c of FIG. 6, in the bioelectrode 26 and the bioelectrode 27, there is very little noise, and it can be seen that the electrocardiogram waveforms equivalent to those of the commercial product (gel electrode) used as a reference are obtained.
Thus, in the bioelectrode of the present invention, it is found that there is no particular difference in the measurement of the electrocardiogram waveform between the bioelectrode subjected to the salt-adding treatment and the bioelectrode without the salt-adding treatment, and that both of these bioelectrodes satisfy the sufficient performance as the bioelectrodes.
Strain Tolerance Evaluation
The bioelectrodes 26 and 27 produced as described above were punched into a size of 20 mm×60 mm. A bending test was conducted in which the surface of the conductive silicone rubber electrode of each bioelectrode was attached onto a conveyor belt illustrated in FIG. 7 and rotated to repeatedly apply deformation (external force). The surface resistance was measured every prescribed number of times, and strain tolerance was evaluated. In addition, a surface resistance change rate was determined based on a surface resistance value before and after the test. The results are listed in Table 4 and FIG. 8.

TABLE 4

| Bio-electrode No. | Presence (P)/ Absence (A) of salt-adding treatment | Surface resistance at the time of physical property evaluation (Ω) | Surface resistance in bending test | | |
|---|---|---|---|---|---|
| | | | Before test (Ω) | After test (10,000 times) (Ω) | Charge rate (times) |
| 26 | P | 0.0328 | 0.0775 | 0.581 | 7.5 |
| 27 | A | 0.0479 | 0.0916 | 2.03 | 22.2 |

Evaluation

According to the results of the physical property evaluation listed in Table 4, it is found that the bioelectrode 26 subjected to the salt-adding treatment has lower surface resistance than the bioelectrode 27 without the salt-adding treatment.

Figure 8:
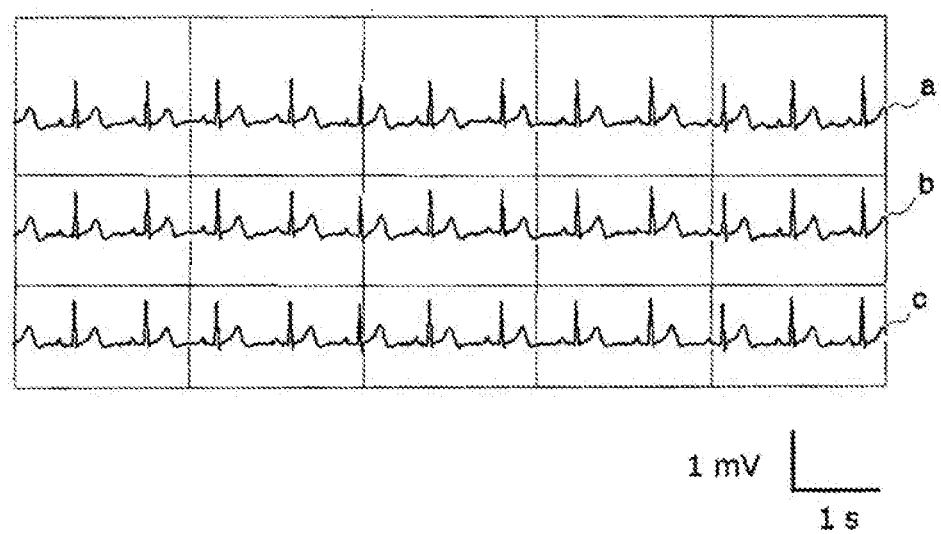
FIG. 8 is a graph illustrating a relation between surface resistance and the number of times of bending in a bending test.

In addition, the graph of FIG. 8 illustrates that the surface resistance of the bioelectrode 26 subjected to the salt-adding treatment does not exceed 1Ω even if the bioelectrode 26 is subjected to the bending test. As listed in Table 4, the surface resistance is 0.581Ω even after 10,000 bending tests. As evaluated in Example 1, if the surface resistance of the bioelectrode is not more than 1Ω, there is very little noise. It can be said that the bioelectrode 26 can be used as a bioelectrode in which there is little noise even after 10,000 bending tests.

The surface resistance change rate of the bioelectrode 27 is 22 times, and the surface resistance change rate of the bioelectrode 26 is 7.5 times, indicating that the strain tolerance is improved by the salt-adding treatment.

The invention claimed is:

1. A bioelectrode comprising a silver coating layer provided on a conductive silicone rubber electrode,
   wherein
   the conductive silicone rubber electrode is composed of a silicone rubber containing conductive carbon particles,
   the silver coating layer is composed of silicone rubber and a silver powder, wherein the silver powder comprises both an agglomerated silver powder and a flake-like silver powder,
   the silver coating layer has electrical conductivity and ionic conductivity,
   the surface of the silver coating layer is brought into contact with a living body,
   ions exist between particles of the silver powder to allow the silver coating layer to have the ionic conductivity,
   the ions are derived from chloride salts of akali metals,
   a content of the flake-like silver powder is 50 parts by weight or more and 180 parts by weight or less with respect to a total parts by weight of the agglomerated silver powder and the flake-like silver powder, and
   the total parts by weight of the combination of the flake-like silver powder and the agglomerated silver powder is 200.

2. The bioelectrode according to claim 1, wherein the silver coating layer has a thickness of 18 μm to 80 μm.

3. The bioelectrode according to claim 1, wherein a flexible printed wiring board is provided as a signal transmission member on a surface opposite to a surface provided with the silver coating layer on the conductive silicone rubber electrode.

* * * * *